Figure 1:
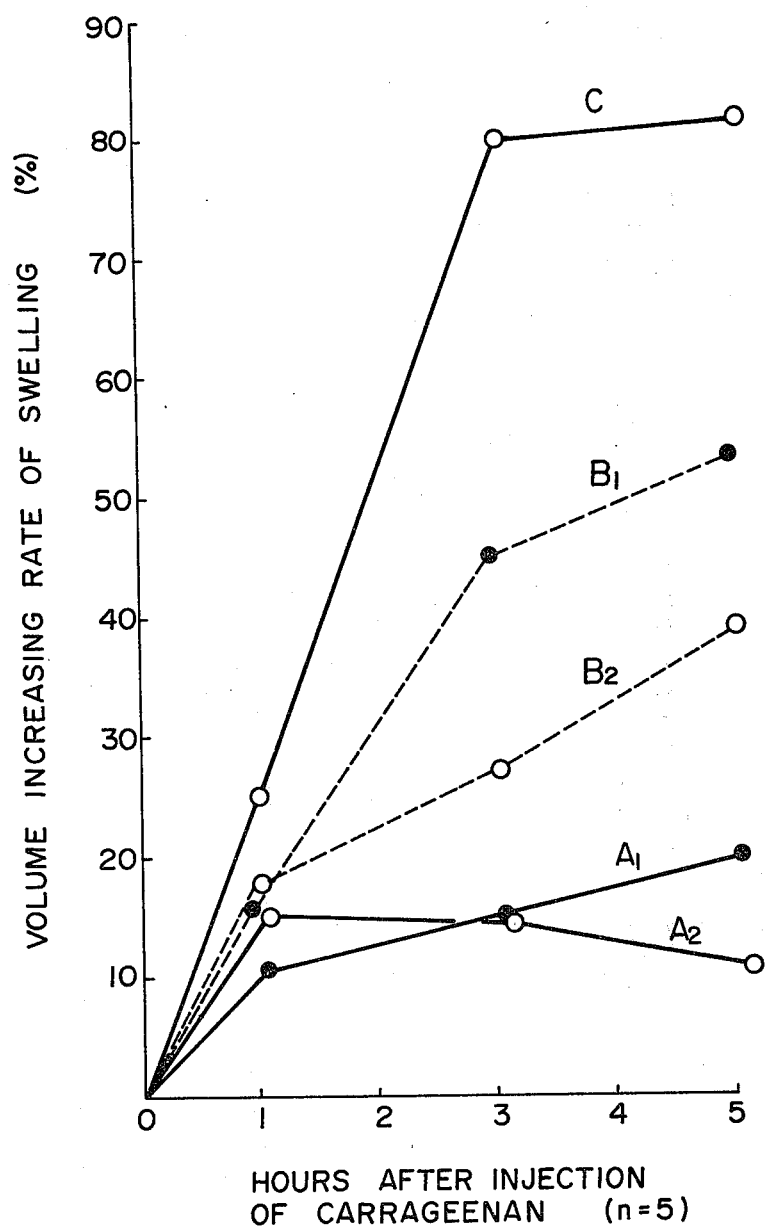

United States Patent [19]

Mizushima et al.

[11] 4,340,594
[45] Jul. 20, 1982

[54] FAT EMULSION CONTAINING STEROID

[75] Inventors: Yutaka Mizushima, Kawasaki; Kazumasa Yokoyama, Toyonaka; Kiichiro Nabeta, Sennan; Noboru Yamada, Ashiya; Tadakazu Suyama, Tsuzuki, all of Japan

[73] Assignee: The Green Cross Corporation, Osaka, Japan

[21] Appl. No.: 260,607

[22] Filed: May 6, 1981

[30] Foreign Application Priority Data

May 15, 1980 [JP] Japan .................................. 55-64875

[51] Int. Cl.³ .............................................. A61K 31/56
[52] U.S. Cl. ..................................... 424/238; 424/243
[58] Field of Search ................................ 424/238, 243

[56] References Cited

U.S. PATENT DOCUMENTS 3,452,014  6/1969  Wright et al. .................. 260/397.45
4,244,942  1/1981  Kamishita et al. .................. 424/243

Primary Examiner—Elbert L. Roberts
Attorney, Agent, or Firm—Cushman, Darby & Cushman

[57] ABSTRACT

A fat emulsion containing a steroid having an anti-inflammatory activity, comprising an effective quantity of a steroid having an anti-inflammatory activity, 5 to 50% (W/V) of soybean oil, a phospholipid in a weight ratio of 1–50 to 100 of said soybean oil, and a proper quantity of water. This fat emulsion exhibits a long-lasting activity in the region of inflammation and is especially useful in the therapeutic or prophylactic treatment of rheumatism, immunological hemolytic anemia, idiopathic thrombocytopenic purpura, and Paget disease, or in conjunction with kidney transplantation.

6 Claims, 6 Drawing Figures

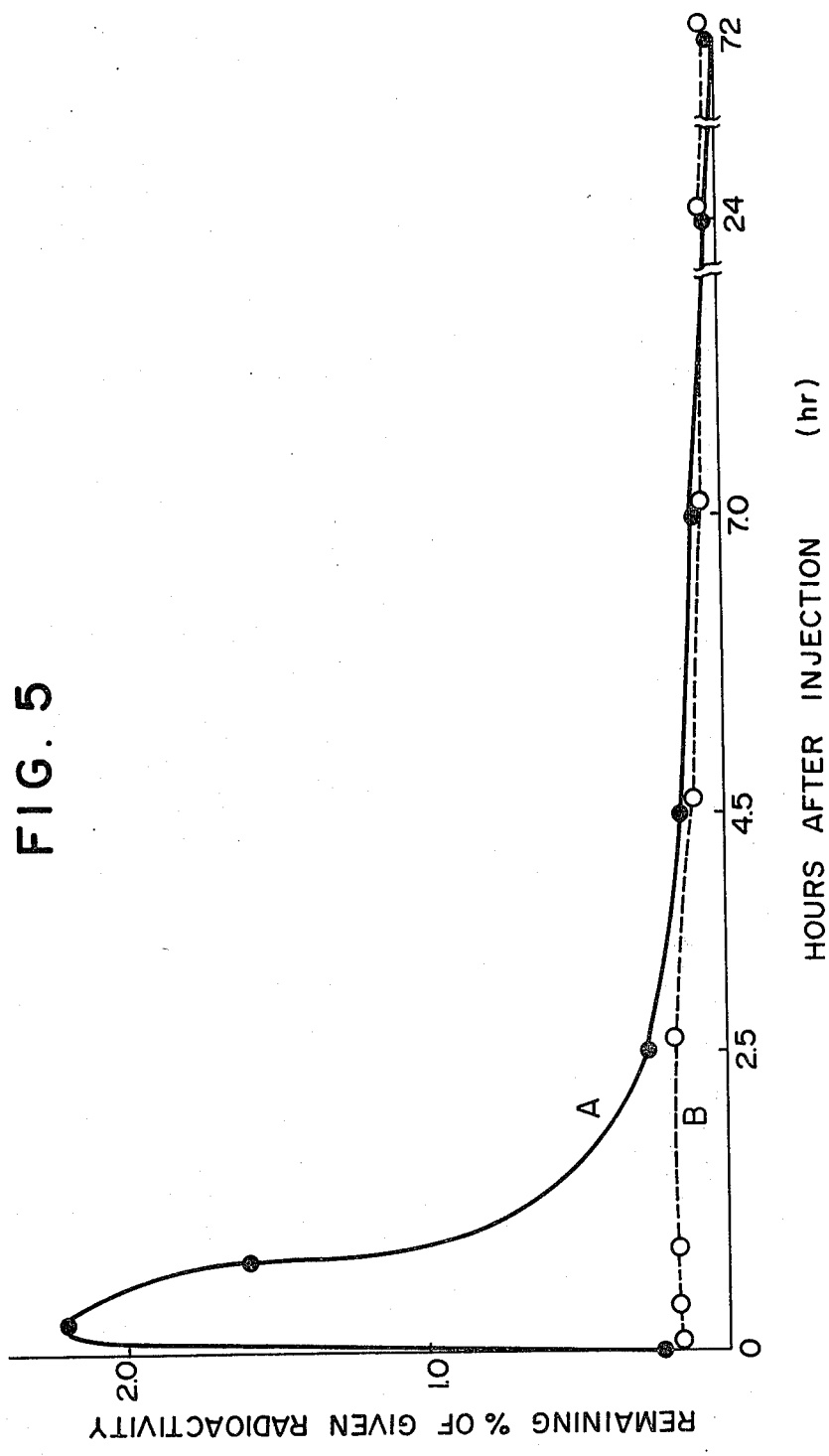

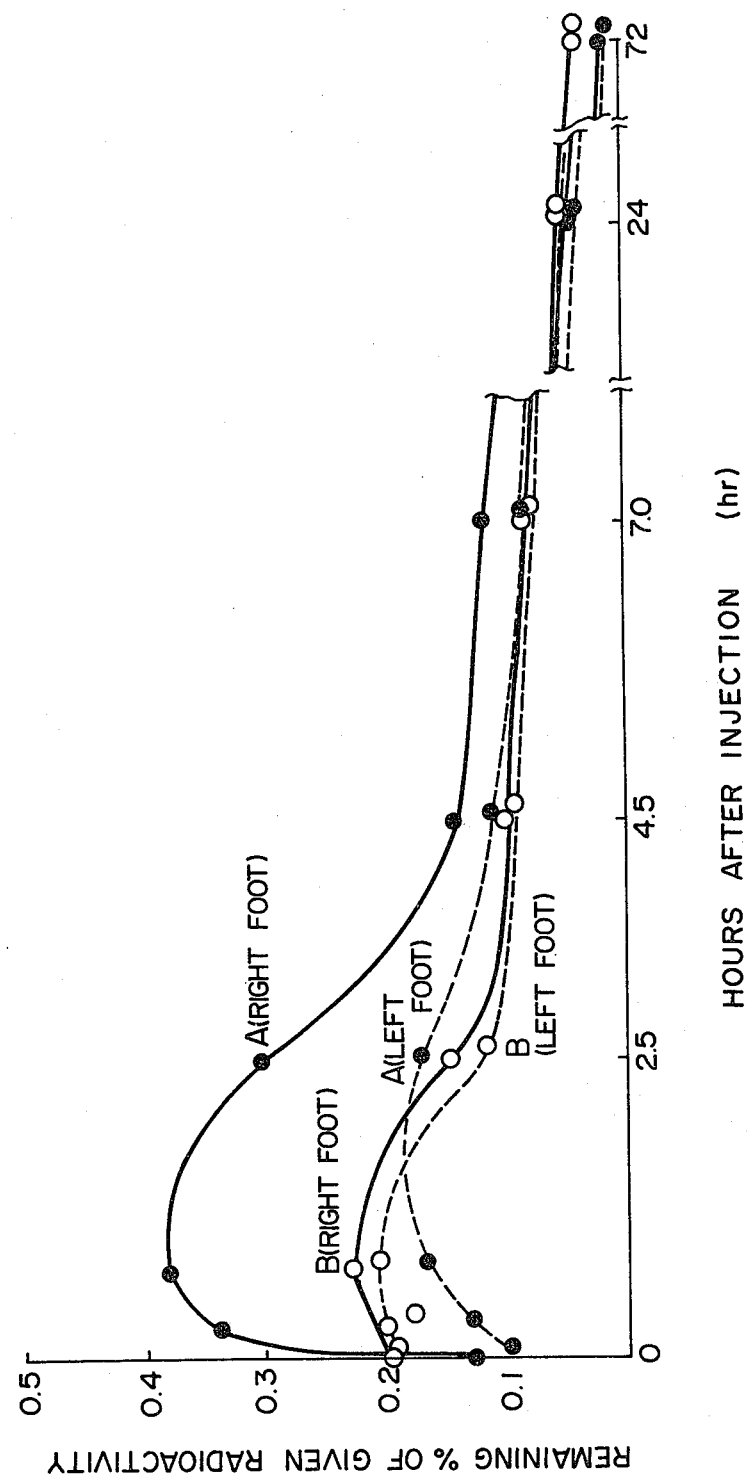

FAT EMULSION CONTAINING STEROID

This invention relates to a fat emulsion containing a steroid having an anti-inflammatory activity.

Because of their widely accepted effectiveness, steroid preparations have been in frequent use in the form of ointment, a muscular injection, or tablet in treating inflammation caused by rheumatism or the like. The continued administration of these drugs, however, brings about various side effects such as osteoporsis, leucocytosis, skin allergy, peptic ulcer, glossy skin, eosinopenia, etc. and in recent years there is a tendency to reappraise the steroid therapy itself.

The side effects caused by the steroid originate from the continued administration of a large dose of steroid in such a case as treatment of rheumatism which requires an extended period of treatment. If there is developed a pharmaceutical preparation capable of exhibiting a strong and sustained effect with the administration of a small dose, the side effects due to administration of steroids may be markedly diminished.

The present inventors carried out extensive investigations to overcome the aforementioned difficulties and, as a result, found that a fat emulsion comprising an anti-inflammatory steroid, soybean oil, a phospholipid and a proper quantity of water manifests a distinguished anti-inflammatory activity and does not exhibit such side effects as are exhibited by the conventional steroid preparation. Based on this finding, the present invention has been accomplished.

An object of this invention is to provide a fat emulsion of an anti-inflammatory steroid.

Another object of this invention is to provide a fat emulsion of a steroid, which shows no side effects in parenteral or oral administration.

A further object of this invention is to provide a novel fat emulsion of an anti-inflammatory steroid, which emulsion exhibits a longer-lasting steroid activity and permits higher concentration of the steroid in the region of inflammation, as compared with the conventional steroid preparation.

Other objects and advantages of this invention will become apparent from the following description.

According to this invention, there is provided a fat emulsion having an anti-inflammatory activity, comprising an effective quantity of an anti-inflammatory steroid, 5 to 50% (W/V), preferably 8 to 30% (W/V), of soybean oil, a phospholipid in a weight ratio of 1–50, preferably 5–30, to 100 of said soybean oil, and a proper quantity of water. The fat emulsion of this invention is useful in the therapeutic or prophylactic treatment of rheumatism, immunological hemolytic anemia, idiopathic thrombacytopenic purpura and Paget disease, or in conjunction with kidney transplantation.

In the accompanying drawings representing the characteristics of the present fat emulsion, FIGS. 1 to 6 show respectively the sustained release effect, time relationships of elimination from the blood, from the muscle, from the liver, and from the spleen, and the time relationship of accumulation in the region of inflammation.

The fat emulsion of this invention may further contain as auxiliary emulsifier 0.3% (W/V) or less of a fatty acid having 6 to 22, preferably 12 to 20, carbon atoms or a physiologically acceptable salt thereof and as stabilizer 0.5% (W/V) or less, preferably 0.1% (W/V) or less, of cholesterol, or 5% (W/V) or less, preferably 1% (W/V) or less, of phosphatidic acid.

Further, the present fat emulsion may be compounded, as stabilizer, with a high molecular substance selected from albumin, dextran, vinyl polymers, nonionic surface active agents, gelatin, and hydroxyethylstarch. The amount to be added of such a stabilizer is 0.1 to 5, preferably 0.5 to 1, part by weight for 1 part by weight of the anti-inflammatory steroid. The albumin is preferably that of human origin when the fat emulsion is intended for use in man. The examples of vinyl polymers which can be used include polyvinylpyrrolidone and polyvinylchloride. Examples of suitable nonionic surface active agents are polyalkylene glycols (for example, polyethylene glycol having an average molecular weight of 1,000 to 10,000, preferably 4,000 to 6,000), polyoxyalkylene copolymers (for example, polyoxyethylenepolyoxypropylene copolymer having an average molecular weight of 1,000 to 20,000 preferably 6,000 to 10,000), polyoxyalkylene derivatives of hydrogenated castor oil [for example, polyoxyethylene (40), polyoxyethylene (20) or polyoxyethylene (100) ether of hydrogenated castor oil], and polyoxyalkylene derivatives of castor oil [for example, polyoxyethylene (40), polyoxyethylene (100) or polyoxyethylene ether of castor oil]. For the purpose of isotonization, it is also possible to add a customary isotonizing agent such as glycerol or glucose.

The fat emulsion of an anti-inflammatory steroid provided by the present invention is a novel pharmaceutical preparation and is a stable fat emulsion in which the particles of fatty oil containing an anti-inflammatory steroid are as fine as $1.0\mu$ or below in diameter.

The fat emulsion of this invention is preferably administered parenterally. Although depending upon the route of administration, the dosage form, and the severity of the disease, the dose of the emulsion is generally 10 to 1,000 ml each time for the adult.

The soybean oil being used in the present fat emulsion is generally a highly pure soybean oil, preferably such as that obtained, for example, by further purifying a purified soybean oil by the method of steam distillation to a purity of 99.9% or above in terms of the sum of triglyceride, diglyceride and monoglyceride [cf. H. J. Lips, J. Am. Oil Chemist, Soc., 27, 422–423 (1950)].

The phospholipid used in this invention is generally a purified one which may be prepared by the customary fractionation with an organic solvent, as shown in the following example.

Into 200 ml of cold n-hexane and 100 ml of cold acetone, is dissolved 130 g of crude yolk phospholipid. To the solution, is added slowly with stirring 1,170 ml of cold acetone. The insolubles are separated by filtration and redissolved in 260 ml of cold n-hexane and 130 ml of cold acetone. To the solution, while being stirred, is added 1,170 ml of cold acetone. The insolubles are separated by filtration and freed from the solvent by distillation to obtain 60 g of a dried substance. This substance contains 70 to 80% of phosphatidylcholine, 12 to 25% of phosphatidylethanolamine, and other phospholipids including phosphatidylinositol, phosphatidylcerine and sphingomyelins [D. J. Hanahan et al., J. Biol. Chem., 192, 623–628 (1951)].

The fatty acid having 6 to 20 carbon atoms which is used as the auxiliary emulsifier can be any of those which are allowed to use in drugs. Such a fatty acid may be of either straight or branched chain, though the former is preferred. A natural fatty acid is convenient for use. Examples of preferred fatty acids are stearic acid, oleic acid, linolic acid, palmitic acid, linolenic acid, and myristic acid. The salt of these fatty acids which may be used is a physiologically acceptable salt such as, for example, an alkali metal salt (e.g. sodium salt and potassium salt) or an alkaline earth metal salt (e.g. calcium salt).

The cholesterol and phosphatidic acid which may be used are those allowed to use in drugs.

The anti-inflammatory steroids suitable for use in the present emulsion are those which are suitable for use as a remedy for inflammation and which may, of course, have other physiological activities such as immunosuppressive activity. The most preferred steroids are those which have a highly lipophilic group and are insoluble in water. Typical examples of such steroids include esters of hydrocortisone with fatty acids of 6 to 22 carbon atoms, esters of prednisolone with fatty acids of 6 to 22 carbon atoms, and esters of dexamethasone with fatty acids of 6 to 22 carbon atoms, such as, for example, dexamethasone palmitate, dexamethasone stearate, dexamethasone myristate, hydrocortisone palmitate, hydrocortisone stearate, hydrocortisone myristate, prednisolone palmitate, prednisolone stearate and prednisolone myristate.

The effective quantity of the anti-inflammatory steroid contained in the present fat emulsion varies with the type and use of the particular emulsion, but is generally 0.01 to 10, preferably 0.1 to 5, %(W/V) based on the emulsion.

The fat emulsion of this invention is prepared by means of a common homogenizer such as, for example, pressure jet homogenizer or supersonic homogenizer. At first, predetermined quantities of soybean oil, a phospholipid, an anti-inflammatory steroid, and, if necessary, a stabilizer such as cholesterol or phosphatidic acid are mixed together and heated to form a solution. The solution is homogenized by using the said homogenizer to form a water-in-oil dispersion which is then transformed into an oil-in-water emulsion by treating together with water in the said homogenizer [cf. R. P. Geyer et al., J. Am. Oil Chem. Soc., 32, 365–370 (1950)]. The stabilizer and an isotomizing agent can be added to the emulsion thus formed.

The invention is illustrated below in detail with reference to Experimental Examples and Examples, but the invention is not limited thereto.

Experimental Example 1

The $LD_{50}$ value in rat of the present fat emulsion prepared as in Example 1 (described later) was 200 ml or more per kg of body weight for a 10% fat emulsion and 150 ml or more per kg of body weight for a 20% fat emulsion. In the cases of both emulsions, entirely no hemolysis was observed on installation at a normal rate.

Experimental Example 2 (Acute toxicity)

Using dd strain mice (female and male, 14 to 17 g in body weight) as test animal, $LD_{50}$ values of dexamethasone palmitate and dexamethasone phosphate (control) were determined. The dexamethasone palmitate was intravenously injected in the form of a fat emulsion prepared as in Example 1 (described later) and the control in the form of an aqueous solution. The $LD_{50}$ value expressed in mg of steroid per kg of body weight was 580 (male) and 420 (female) for dexamethasone palmitate, while that for the control was 140 (male) and 115 (female), indicating a high safety level of dexamethasone palmitate.

Experimental Example 3

The time relationship of sustained action of the present fat emulsion in vivo was compared with that of a control. A fat emulsion of dexamethasone palmitate prepared as in Example 1 (described later) and an aqueous solution of dexamethasone phosphate (control) were used. The test animal was Wistar rat (each group consisting of 5 males, about 180 g in body weight) and the medicines were intravenously administered. For the evaluation, carrageenan edema was induced in rat by administering 0.1 ml of a 1% carrageenan solution in physiological saline into the ringworm of feet of the kind paw and 18 hours after the carrageenan administration 3 mg/kg or 30 mg/kg of the medicine was administered through the vena coccygea. The effect of the medicine was traced by determining the swelling of the kind paw at predetermined time intervals. The results were as shown in FIG. 1, in which the lines $A_1$ and $A_2$ represent the cases of dexamethasone palmitate (3 mg/kg and 30 mg/kg), $B_1$ and $B_2$ the cases of dexamethasone phosphate (3 mg/kg and 30 mg/kg), and C the case of saline, respectively. As is understandable from FIG. 1, as compared with the aqueous solution used as control, the fat emulsion of dexamethasone palmitate exhibited significant sustained release effect and more accumulation in the inflammation region.

Experimental Example 4

A comparative experiment was conducted about the accumulation of the present preparation in the inflammatory region. The administered medicines were a fat emulsion and an aqueous solution as in Experimental Example 2. The test animal was Wistar rat (each group consisting of 4 males, 180 g in each body weight). Each rat was administered with 0.1 ml of a 1% carrageenan solution in physiological saline into the ringworm of feet of one of the kind paw. Thirty minutes after the administration of carrageenan each rat was administered through vena coccygea with the medicine labelled with 3H. At predetermined time intervals, various internal organs and tissues were excised or trimmed away to determine their radioactivity with a liquid scintillation counter. The medicines were labelled with 3H at 6- and 7-positions. Each rat was administered with 0.3 mg (30 μC in radioactivity) of the medicine per kg at a rate of 1 ml/minute/100 g body weight.

The results obtained were shown in FIGS. 2 to 6, in which the line A represents the case of dexamethasone palmitate and B the case of dexamethasone phosphate, respectively.

Figure 2:
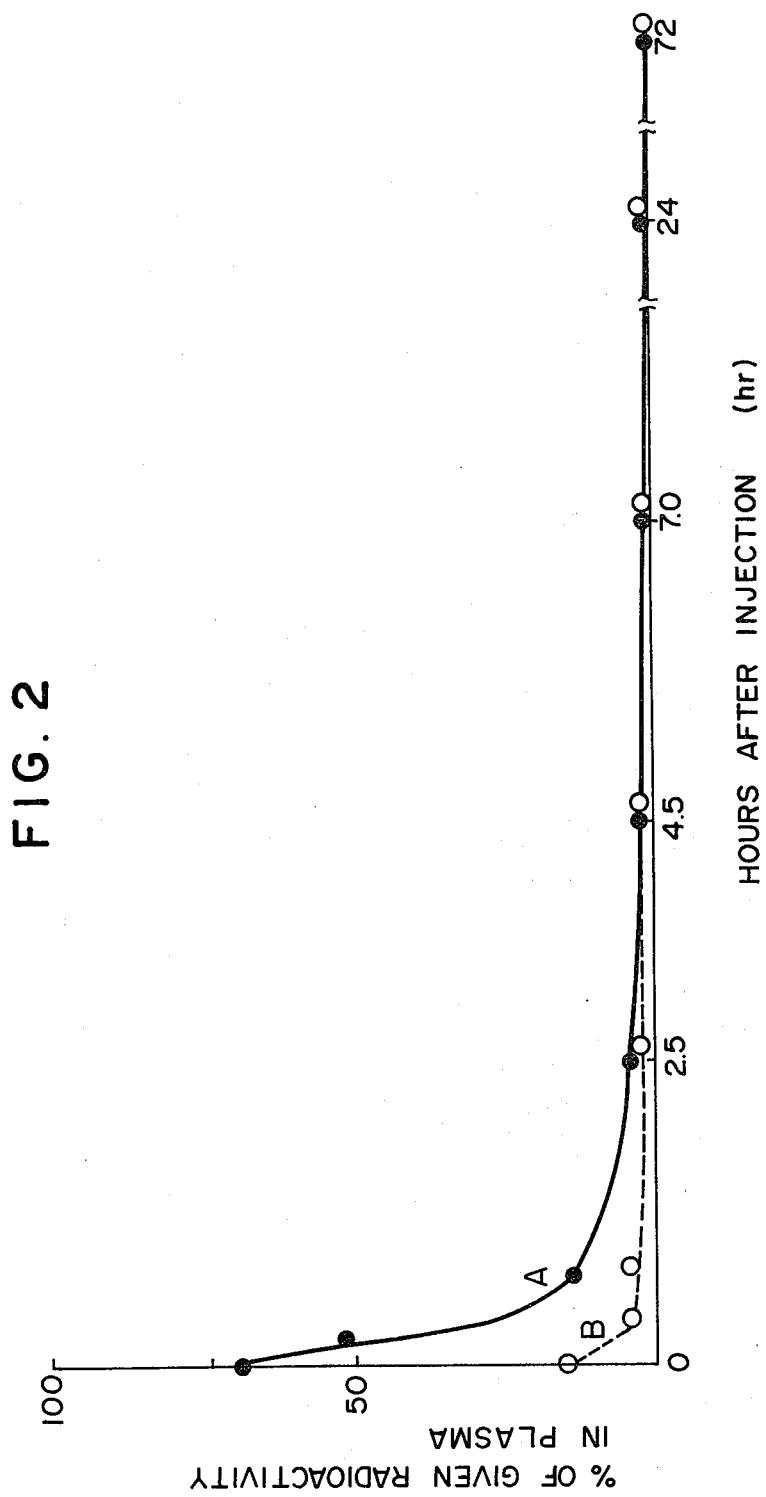

The time relationship of the elimination of the medicine from the blood was as shown in FIG. 2. It is seen that as compared with the aqueous solution, more of the fat emulsion of this invention is retained by the blood during 2 hours after the administration.

Figure 3:
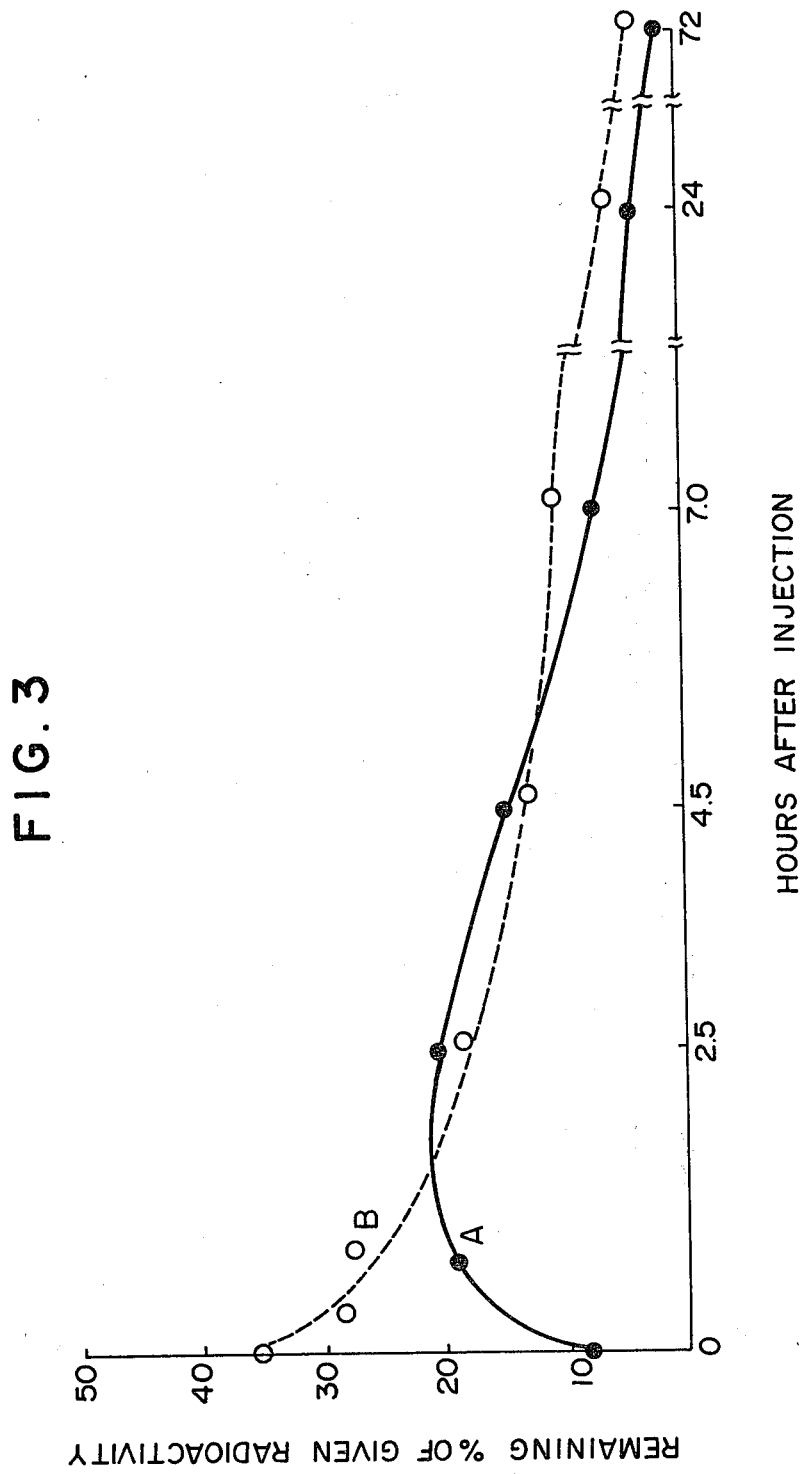

The accumulation in the muscle was as shown in FIG. 3. During two hours after the administration, both medicines behaved in opposite ways.

Figure 4:
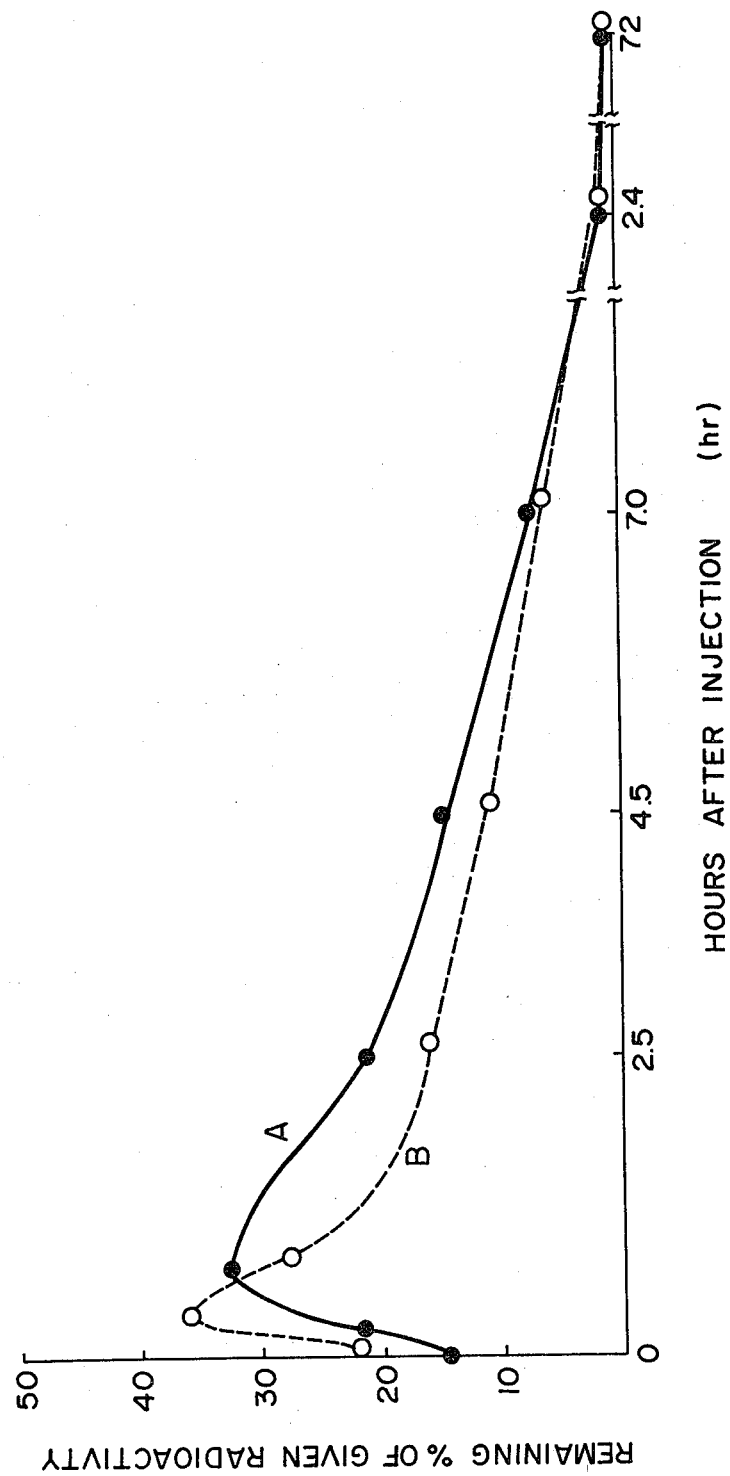

The accumulation in the liver was as shown in FIG. 4. The elimination curve of the present preparation shifted toward the right along the time axis.

The accumulation in the spleen was as shown in FIG. 5. As contrasted to the control, the initial drug uptake of the spleen was markedly high in the case of the fat emulsion. This fact indicates a rapid action of the present preparation upon the antibody production system and suggests its usefulness in the transplantation of kidney and the like.

The accumulation in the inflammatory region was as shown in FIG. 6. The right foot swelled by the action of carrageenan, while the left foot served as a control. In 2.5 hours after the administration, the concentration of the present preparation in the inflammatory region became about 2 to 3 times as large as that in the noninflammatory region, whereas such a specific uptake was not noticed in the case of the water-soluble medicine.

Example 1

To 100.0 g of purified soybean oil, were added 24.0 g of purified yolk phospholipid, 20 g of dexamethasone palmitate, 0.5 g of sodium oleate and 0.5 g of phosphatidic acid. The resulting mixture was heated at 40° to 75° C. to form a solution. After addition of 1,000 ml of distilled water, the mixture was emulsified by passing through a Manton-Gaulin Homogenizer 10 times under a first stage pressure of 100 kg/cm$^2$ and a total pressure of 450 kg/cm$^2$. The emulsion was admixed with 5.0 g of glycerol followed by 400 ml of distilled water for injection at 20° to 40° C. The mixture was roughly emulsified in a Homomixer. The resulting coarse emulsion was homogenized by passing 10 times through the Manton-Gaulin homogenizer under a first stage pressure of 120 kg/cm$^2$ and a total pressure of 500 kg/cm$^2$. There was obtained a homogenized fine fat emulsion containing an anti-inflammatory steroid. The average particle size of the emulsion was 0.2 to 0.4μ and the emulsion contained no particles having a size greater than 1μ.

Example 2

A fat emulsion containing an anti-inflammatory steroid was obtained by repeating the procedure of Example 1, except that the sodium oleate was not added.

Example 3

A fat emulsion containing an anti-inflammatory steroid was prepared by repeating the procedure of Example 1, except that 0.5 g of cholesterol was added in place of the phosphatidic acid.

Example 4

A mixture was prepared from 50 g of purified soybean oil, 6 g of purified yolk phospholipid, 0.25 g of sodium oleate, 0.25 g of phosphatidic acid, and 2.0 g of hydrocortisone palmitate. The mixture was treated in a manner similar to that in Example 1 to obtain a fat emulsion containing an anti-inflammatory steroid.

Example 5

A fat emulsion containing an anti-inflammatory steroid was prepared by repeating the procedure of Example 1, except that prednisolone palmitate was added in place of the dexamethasone palmitate.

Example 6

A solution was prepared by mixing together 20 g of purified soybean oil and 4 g of dexamethasone stearate and heating at 80°. To the solution was added 5 g of purified yolk phospholipid and the mixture was heated at 80° C. with vigorous stirring to form a solution. After addition of 200 ml of distilled water, the mixture was stirred in a Homomixer to form a coarse emulsion. The coarse emulsion was homogenized by means of a Manton-Gaulin homogenizer under application of a high pressure to obtain a fine fat emulsion containing an anti-inflammatory steroid.

What is claimed is:

1. A fat emulsion containing a steroid having an anti-inflammatory activity comprising an effective quantity of a steroid having an anti-inflammatory activity selected from the group consisting of esters of hydrocortisone with fatty acids of 6 to 22 carbon atoms, esters of prednisoline with fatty acids of 6 to 22 carbon atoms, and esters of dexamethasone with fatty acids of 6 to 22 carbon atoms, 5 to 50% (W/V) of soybean oil, a phospholipid in a weight ratio of 1–50 to 100 of said soybean oil, and a proper quantity of water.

2. A fat emulsion according to claim 1, wherein the steroid having an anti-inflammatory activity is dexamethasone palmitate, dexamethasone stearate, dexamethasone myristate, hydrocortisone palmitate, hydrocortisone stearate, hydrocortisone myristate, prednisolone palmitate, prednisolone stearate, or prednisolone myristate.

3. A fat emulsion according to claim 1, which contains glucose or glycerine as an isotonizing agent.

4. A fat emulsion according to claim 1, wherein the fat emulsion contains, as an auxiliary emulsifier or an emulsion stabilizer, up to 0.3% (W/V) of a fatty acid having 6 to 22 carbon atoms or a physiologically acceptable salt thereof.

5. A fat emulsion according to claim 1, wherein the fat emulsion contains as a stabilizer 0.5% (W/V) or less of cholesterol or 5% (W/V) or less of phosphatidic acid.

6. A fat emulsion according to claim 1, wherein the fat emulsion contains as a stabilizer at least one member selected from the group consisting of albumin, dextran, vinyl polymers, nonionic surface active agents, gelatin, and hydroxyethylstarch.

* * * * *